United States Patent
Bagger-Sjöbäck et al.

(10) Patent No.: US 8,029,487 B2
(45) Date of Patent: Oct. 4, 2011

(54) ABSORBENT ARTICLE WITH IMPROVED FIT AND LEAKAGE SECURITY

(75) Inventors: Anna Bagger-Sjöbäck, Göteborg (SE); Evelien Beuling, Sävedalen (SE); Solgun Drevik, Mölnlycke (SE)

(73) Assignee: SCA Hygiene Products AB, Göteborg (SE)

( * ) Notice: Subject to any disclaimer, the term of this patent is extended or adjusted under 35 U.S.C. 154(b) by 270 days.

(21) Appl. No.: 12/307,511

(22) PCT Filed: Mar. 28, 2007

(86) PCT No.: PCT/SE2007/050192
§ 371 (c)(1),
(2), (4) Date: Jan. 5, 2009

(87) PCT Pub. No.: WO2008/004961
PCT Pub. Date: Jan. 10, 2008

(65) Prior Publication Data
US 2009/0292268 A1 Nov. 26, 2009

(30) Foreign Application Priority Data
Jul. 5, 2006 (GB) .................................. 0613398.7

(51) Int. Cl.
*A61F 13/15* (2006.01)
*A61F 13/20* (2006.01)
(52) U.S. Cl. ............................................... 604/385.201
(58) Field of Classification Search .................. 604/380, 604/385.101, 385.201
See application file for complete search history.

(56) References Cited

U.S. PATENT DOCUMENTS

| 4,765,780 A | 8/1988 | Angstadt |
| 4,886,513 A | 12/1989 | Mason, Jr. et al. |
| 5,795,344 A | 8/1998 | Chappell |
| 2004/0122407 A1 | 6/2004 | Valdividia Hernandez et al. |
| 2005/0182374 A1 | 8/2005 | Zander et al. |

FOREIGN PATENT DOCUMENTS

| EP | 0 249 405 A2 | 12/1987 |
| EP | 0 572 033 A2 | 12/1993 |
| EP | 0 956 844 A2 | 11/1999 |
| EP | 0 969 784 B1 | 1/2000 |

(Continued)

OTHER PUBLICATIONS

PCT/ISA/210, mailed Oct. 26, 2007.

(Continued)

*Primary Examiner* — Melanie Hand
(74) *Attorney, Agent, or Firm* — Buchanan Ingersoll & Rooney PC (57) ABSTRACT

An absorbent article having front, crotch and rear portions and an absorbent core of unitary construction. The core has a first region with two legs extending in the longitudinal direction of the article through at least parts of the crotch portion towards endings in the rear portion. A maximum distance between facing sides of the legs in the transverse direction is, in the crotch portion, located at a position in the longitudinal direction corresponding to a crotch point. Furthermore, the facing sides of the legs converge backwards such that a distance between them is reduced from the maximum distance to a minimum distance in the rear portion. In addition, the core has a second region surrounding the first region and the average density of the core is lower in the second region than in the first region.

17 Claims, 5 Drawing Sheets

FOREIGN PATENT DOCUMENTS

| | | |
|---|---|---|
| EP | 1 102 824 B1 | 5/2001 |
| EP | 1 253 231 A2 | 10/2002 |
| EP | 1 275 358 A2 | 1/2003 |
| EP | 1 458 718 B1 | 9/2004 |
| GB | 2 439 719 A | 1/2008 |
| SE | 9401542-7 | 11/1998 |
| WO | WO 98/27908 | 7/1998 |
| WO | WO 99/27876 A1 | 6/1999 |
| WO | WO 02/085269 A1 | 10/2002 |
| WO | WO 02/085270 A1 | 10/2002 |
| WO | WO 02/087483 A1 | 11/2002 |
| WO | WO 02/087484 A1 | 11/2002 |
| WO | WO 03/047484 A1 * | 6/2003 |
| WO | WO 03047484 A1 * | 6/2003 |
| WO | WO 03/053301 A1 | 7/2003 |
| WO | WO 03/059222 A1 | 7/2003 |
| WO | WO 2006/059922 A1 | 6/2006 |
| WO | WO 2007/008124 A1 | 1/2007 |

OTHER PUBLICATIONS

PCT/ISA/237.

* cited by examiner

ABSORBENT ARTICLE WITH IMPROVED FIT AND LEAKAGE SECURITY

PRIORITY

This application is a national stage application of PCT/SE2007/000458, filed 11 May 2007, which claims priority to GB 0613398.7, filed 5 Jul. 2006.

TECHNICAL FIELD

The present disclosure relates to absorbent articles, such as sanitary towels, panty liners, incontinence pads or diapers which are designed so that they adopt a particular form when in use and so that security against leakage is promoted. Certain regions of the article which are less dense than other regions allow the article to take on a desired form and minimise the problems associated with the article moving out of place on the user's body.

BACKGROUND

As well as good absorptive properties, primary requirements of absorbent articles, such as sanitary towels, panty liners, incontinence pads or diapers, are good fit and leakage security. Various methods have been employed in the design and manufacture of absorbent articles so that they follow the contours of the user's body well and do not move out of place during use.

Patent applications WO 03/053301, EP 0 956 844, WO 03/047484, WO 02/087484, WO 02/085270, WO 03/059222, WO 02/087483, WO 02/085269 and related applications describe absorbent products which comprise a stiffening element that is intended to contribute to the three-dimensional shape of the products during their use.

EP 1 458 718 describes a disposable diaper having a region of low stiffness being a rectangular region along each side edge of the absorbent member. The low bending stiffness of this region allows the diaper to be bent upwards easily to join around the waist of the user.

EP 1 275 358 describes an absorbent article having a front absorbent region and a rear cushion region. The stiffness is higher in the front absorbent region, such that the shape of the raised region is maintained.

US 2004/0122407 discloses a sanitary napkin, the longitudinal central region of which has a higher flexure-resistance than the outer portions. In this way, the side regions are flexible enough that the sanitary napkin forms a cup-like trough under the wearers' genitals.

EP 0 572 033 discloses an absorbent article having zones which vary in stiffness. The article resists bunching and twisting during use. EP 1 102 824 discloses a sanitary napkin, the edges of which are less stiff than the centre for comfort.

There is still room for improvement in the leakage security and fit of absorbent articles such as sanitary napkins. In particular, many of the earlier approaches to this problem involve cutting or otherwise removing parts of the absorbent cores of absorbent articles. However, this reduces the total amount of absorbent material which is present and thus provides lower security against leakage. Furthermore, cutting or otherwise removing parts of the absorbent core often results in wasted material, as the cut-out parts cannot always be used. Furthermore, many known products require additional stiffening elements.

SUMMARY

The present disclosure addresses the problems associated with the art in this area. It provides an improved absorbent article, such as a sanitary towel, a panty liner, an incontinence pad or a diaper, whereby said article has a transverse direction, a longitudinal direction and a longitudinal centre line, whereby said article further has a front portion, a crotch portion and a rear portion, whereby said article comprises an absorbent core of unitary construction, whereby said absorbent core is delimited by a circumferential edge, whereby said absorbent core comprises a first region extending in the longitudinal direction of the article from a position in the front portion, through the crotch portion and at least some way into the rear portion, whereby said first region comprises two legs extending in the longitudinal direction of the article through at least parts of the crotch portion towards separate leg endings in the rear portion, whereby said legs are arranged symmetrically about said longitudinal centre line, whereby a distance between facing sides of the respective legs in the transverse direction varies in the longitudinal direction, whereby a maximum distance between the facing sides of the respective legs in the transverse direction is, in the crotch portion, located at a position in the longitudinal direction corresponding to a position of a crotch point, whereby said facing sides of the respective legs converge backwards in the longitudinal direction such that said distance is reduced from said maximum distance to a minimum distance in the rear portion, whereby said absorbent core further comprises a second region surrounding said first region and extending between said first region and said circumferential edge, and whereby the average density of said absorbent core in said second region is lower than the average density of said absorbent core in said first region.

Particularly, the present disclosure provides an absorbent article which combines the feature of improved leakage security with good fit and correct, secure placement of the article on the wearer. The design of the core improves the inlet and distribution of the liquid to be absorbed. Furthermore, cutting or otherwise removing parts of the absorbent core may be avoided, providing more absorbent material and giving the wearer the impression of a more "complete" article (thus improving wearer confidence). In addition, by avoiding the need to cut or otherwise remove parts of the absorbent core, the material utilization is improved, which leads to improved cost efficiency. The effects of embodiments of the disclosure can be achieved solely through the absorbent core of the article, thus avoiding the need to use additional stiffening elements. The articles of the disclosure may also be manufactured using existing equipment, with only minor modifications to current processes.

Still other objects and features of the present disclosure will become apparent from the following detailed description considered in conjunction with the accompanying drawings. It is to be understood, however, that the drawings are designed solely for purposes of illustration and not as a definition of the limits of the disclosure, for which reference should be made to the appended claims. It should be further understood that the drawings are not necessarily drawn to scale and that, unless otherwise indicated, they are merely intended to conceptually illustrate the structures described herein.

BRIEF DESCRIPTION OF THE DRAWINGS

In the drawings, wherein like reference characters denote similar elements throughout the several views.

DETAILED DESCRIPTION OF PREFERRED EMBODIMENTS

The disclosure will be described in further detail in the following, with reference to the accompanying figures.

As mentioned previously, an embodiment of the disclosure concerns an absorbent article 1, such as a sanitary towel, a panty liner, an incontinence pad or a diaper. Preferably, the absorbent article 1 is a sanitary towel. Such articles are commonly used for acquisition and storage of bodily exudates such as urine, faeces or menstrual fluid. The absorbent article 1 is preferably disposable—i.e. it is intended to be used only once and disposed thereafter, rather than being cleaned and re-used.

Figure 1:
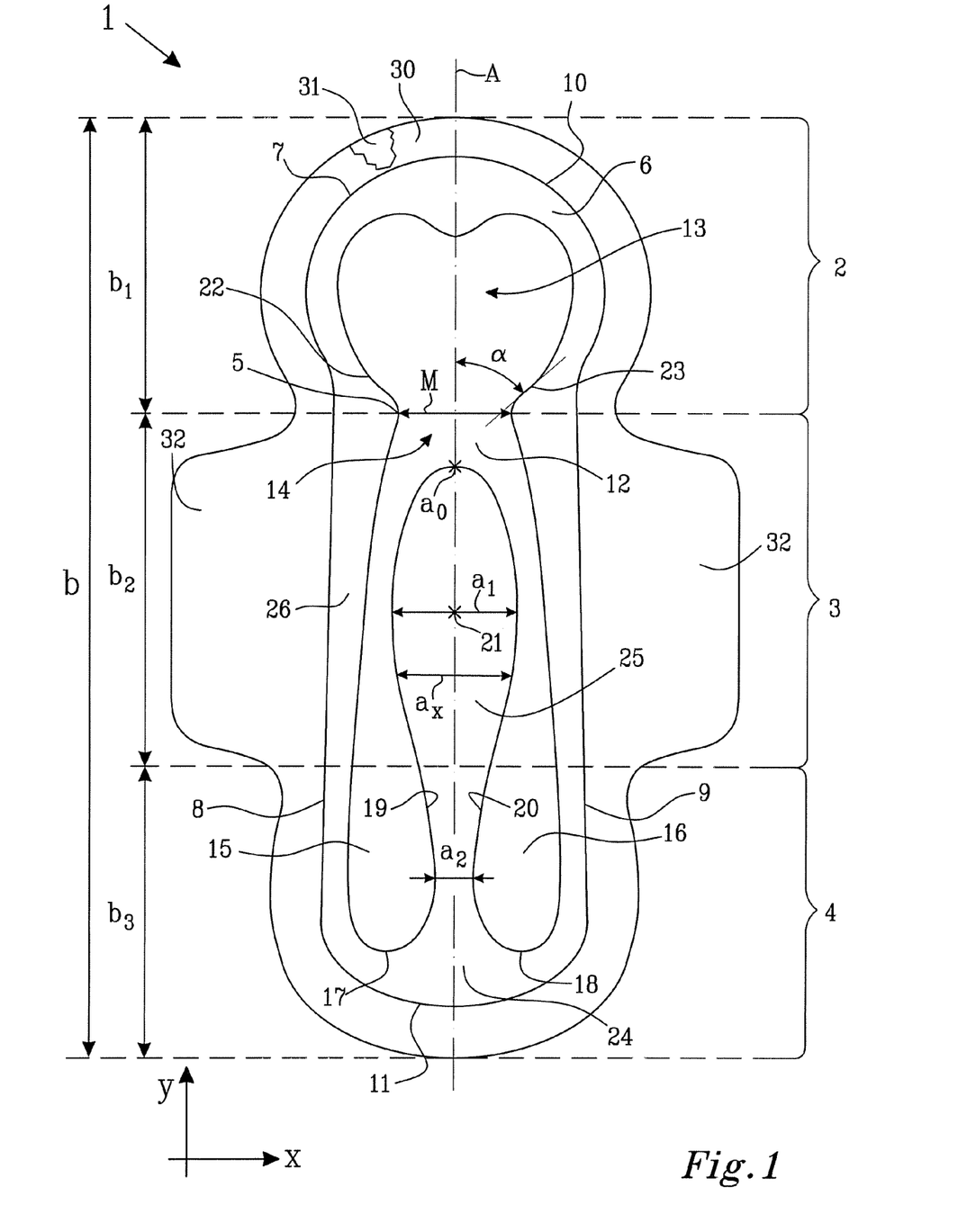
FIG. 1 shows a plan view of a first embodiment of an absorbent article according to the disclosure.

FIG. 1 shows a plan view of a first embodiment of the absorbent article 1 according to an embodiment of the present disclosure. The absorbent article 1 shown in FIG. 1 is a sanitary towel. The article 1 has a transverse direction x, a longitudinal direction y and a longitudinal centre line A as indicated. The total length of the article 1 in the longitudinal direction is length b.

The article 1 further has a front portion 2, a crotch portion 3 and a rear portion 4 arranged in the article's longitudinal direction as well as a transition 5 between the front portion 2 and the crotch portion 3. In use, the front portion 2 of the article 1 is intended to cover the pubic region of the wearer. The front portion 2 is defined by the front transverse edge of the article 1. Furthermore, the front portion 2 extends a certain length b1 along the article 1 in the longitudinal direction. In a sanitary napkin of the type shown, the front portion 2 has a length b1 in the longitudinal direction which is between 10-50%, more preferably between 20-40%, most preferably between 25-35% of the total length b of the article 1.

The crotch portion 3 of the article 1 is located adjacent to the front portion 2 in the longitudinal direction. In use, the crotch portion 3 lies between the legs of the user and covers the user's genital region. In a sanitary napkin of the type shown, the crotch portion 3 has a length b2 in the longitudinal direction which is between 10-50%, more preferably between 25-45%, most preferably between 30-40% of the total length b of the article. Typically, the length b2 of the crotch portion 3 in the longitudinal direction is between 40-110 mm, more preferably between 50-105 mm, most preferably between 85-100 mm. The transition 5 between the front portion 2 and the crotch portion 3 is the border area between the front and crotch portions 2, 3.

The rear portion 4 is located at the opposite end of the article 1 from the front portion 2 and is located adjacent to the crotch portion 3 in the longitudinal direction. In use, the rear portion 4 extends towards the user's rear. The rear portion 4 is defined by the rear transverse edge of the article 1 and extends a certain length b3 along the article 1 in the longitudinal direction. In a sanitary napkin of the type shown, the rear portion 4 has a length b3 in the longitudinal direction which is between 15-55%, more preferably between 25-45%, most preferably between 30-40% of the total length b of the article 1.

Furthermore, the absorbent article 1 according to an embodiment of the disclosure comprises an absorbent core 6 of unitary construction. The "absorbent core" is the absorbent structure of the article 1 which acquires and stores bodily fluids. The absorbent core 6 may be of any conventional kind. Examples of commonly occurring absorbent materials are cellulosic fluff pulp, tissue, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred superabsorbent materials are further surface cross-linked so that the outer surface or shell of the superabsorbent particle, fibre, flake, sphere, etc. possesses a higher crosslink density than the inner portion of the superabsorbent. The superabsorbent materials may be in any form suitable for use in absorbent composites including particles, fibres, flakes, spheres, and the like. A high absorption capacity is provided by the use of high amounts of superabsorbent material.

The thin absorbent bodies, which are common in for example baby diapers and incontinence guards, often comprise a compressed, mixed or layered structure of cellulosic fluff pulp and superabsorbent polymers. The size and absorbent capacity of the absorbent core 6 may be varied to suit different users, such as infants or adult incontinent persons.

The phrase "unitary construction" in the present context is intended to mean that the absorbent core 6 is constructed from essentially one type of material, this being essentially the same material, or essentially the same combination of two or more materials throughout the absorbent core 6. Variations in density and concentration of the material may occur, but these are limited to those which may be obtained without incorporation of regions which have been formed separately and then physically joined to each other. For example, when the absorbent core 6 comprises a matrix of hydrophilic fibres and superabsorbent material as described above, the relative concentrations of superabsorbent material and fibres may be different in different parts of the core 6. However, the absorbent core 6 should not, for instance, comprise layers or laminates of different composition. Likewise, variations in the density or concentration of various components across the longitudinal direction, the transverse direction or the thickness direction of the absorbent core 6 are acceptable, yet the core 6 should not comprise areas or layers of different composition which are formed separately and later joined together. Examples of methods for production of the absorbent core 6 according to the disclosure will be described below.

Furthermore, the absorbent core 6 is delimited by a circumferential edge 7 comprising a pair of opposing longitudinal edges 8, 9 and a pair of opposing transverse edges 10, 11. The absorbent core 6 does not necessarily have a parallelogram shape, but may have e.g. rounded edges or a dog-bone shape. In this case, the transition between transverse and longitudinal edges is defined as the point on the edge of the core at which the rate of curvature of the transverse edge of the core with respect to the transverse direction is greatest. In a preferred embodiment, the longitudinal edges of the core are substantially parallel.

In addition, the absorbent core 6 comprises a first region 12 which extends in the longitudinal direction y of the article 1 from a position in the front portion 2, through the crotch portion 3 and a considerable way into the rear portion 4. The first region 12 is designed and arranged such that it is symmetric about the longitudinal centre line A of the article 1. This is important so that the article 1 lies symmetrically on the user's body when in use. By the expression "symmetric about the longitudinal centre line A" it is herein meant that each point in the first region 12 on one side of the longitudinal centre line A has a corresponding point in the first region 12 on the other side of the longitudinal centre line A; the two points being related to each other by reflection in a plane located on the longitudinal centre line A. The part of the first region 12 located on one side of the longitudinal centre line A is therefore the mirror image of the part of the first region 12 located on the other side of the longitudinal centre line A.

As will be further described below, the average density of the absorbent core 6 is higher in the first region 12 than in the other regions of the absorbent core 6. Thus, the absorbent core 6 is stiffer in the first region 12 than in the other regions of the absorbent core 6.

In the first embodiment shown in FIG. 1, the first region 12 comprises a head part 13 in the front portion 2, an intermediate part 14 in the crotch portion 3 and two legs 15, 16 extending in the longitudinal direction y of the article 1 from the intermediate part 14, through the remainder of the crotch portion 3 towards separate leg endings 17, 18 in the rear portion 4. Thus, the two legs 15, 16 extend through a considerable part of the crotch portion 3 towards the separate leg endings 17, 18. The head part 13 is joined to the intermediate part 14 at the transition 5. In accordance with the above described, the head part 13 and the intermediate part 14 are symmetric about the longitudinal centre line A. Furthermore, the two legs 15, 16 are arranged symmetrically about the longitudinal centre line A of the article 1.

Furthermore, each leg 15, 16 has a side 19, 20, i.e. an edge, facing the other leg 15, 16. The distance $a_x$ between the facing sides 19, 20 of the respective legs 15, 16 in the transverse direction x of the absorbent article 1 varies along the longitudinal direction y of the article 1 in the crotch portion 3 and in the rear portion 4. That is, the edges of the respective legs 15, 16 lying closest to the longitudinal centre line A, i.e. the facing sides 19, 20, are not parallel with the longitudinal centre line A. The distance $a_x$ therefore exhibits maxima and minima along the longitudinal direction of the article 1. Preferably, the distance $a_x$ varies continuously along the longitudinal direction of the article 1.

According to the disclosure, a maximum distance $a_1$ in the transverse direction between the facing sides 19, 20 of the respective legs 15, 16 is, in the crotch portion 3, located at a position in the longitudinal direction of the article 1 corresponding to a position of a crotch point 21. Thus, when a line is drawn in the transverse direction between the facing sides 19, 20 at the position in the crotch portion 3 where the maximum distance $a_1$ is located, the line crosses the crotch point 21. The "crotch point" is as defined in EP-B1-0 969 784 and described further in the international application PCT/SE2004/001759. It is determined by placing the article on the wearer in a standing position, and then placing an extensible filament around the legs of the wearer in a figure-of-eight configuration. The point on the article 1 corresponding to the point of intersection of the filament is deemed to be the crotch point 21. It should be understood that the crotch point 21 is determined by placing the absorbent article 1 on the wearer in the intended manner and determining where the crossing point of the filament would cross the article/core.

For example, the maximum distance $a_1$ in the crotch portion 3 may be 10-50 mm.

Furthermore, according to the disclosure the facing sides 19, 20 of the respective legs 15, 16 converge backwards in the longitudinal direction of the article 1 such that the distance $a_x$ between the facing sides 19, 20 of the respective legs 15, 16 in the transverse direction x is reduced from the maximum distance $a_1$ in the crotch portion 3 to a minimum distance $a_2$ in the rear portion 4. In other words, the facing sides 19, 20 of the respective legs 15, 16 converge in a backward direction of the article 1 from the position in the longitudinal direction where the maximum distance $a_1$ is located to the position in the longitudinal direction where the minimum distance $a_2$ is located.

For example, the minimum distance $a_2$ in the rear portion 4 may be 5-30 mm, more preferably 10-20 mm, most preferably 10-15 mm.

In the first embodiment shown in FIG. 1, the facing sides 19, 20 of the respective legs 15, 16 also converge forwards in the longitudinal direction such that the distance $a_x$ between the facing sides 19, 20 of the respective legs 15, 16 is reduced from the maximum distance $a_1$ in the crotch portion 3 to a zero distance in the crotch portion 3. In other words, the facing sides 19, 20 of the respective legs 15, 16 converge in a forward direction of the article 1 from the position in the longitudinal direction where the maximum distance $a_1$ is located to a position in the longitudinal direction where the two facing sides 19, 20 meet. Thus, in the first embodiment the two facing sides 19, 20 of the respective legs 15, 16 are joined in the crotch portion 3 (i.e. at the intermediate part 14). The position where the two facing sides 19, 20 are joined is denoted $a_0$.

Since the facing sides 19, 20 of the two legs 15, 16 are joined in the crotch portion 3 in the first embodiment, the first region 12 does not comprise any legs in the transition 5 nor in the front portion 2 in this embodiment.

Furthermore, in the first embodiment shown in FIG. 1, the first region 12 has a width M in the transverse direction at the transition 5 between the front portion 2 and the crotch portion 3. The width M is adapted to the distance between two particular muscle tendons on both sides of the crotch of the wearer directly in front of the groins. These muscle tendons form part of the muscle group which originates on the inside of the pelvic diaphragm and has its attachment along the thigh. This muscle group consists of the adductor muscles, especially gracilis. It is known that the distance between said two muscle tendons is very similar for all people: around 25-45 mm. In around 80% of women, the distance between the two muscle tendons is approximately 30-32 mm. The term "transition between the front portion and the crotch portion" is herein intended to mean the region which in the intended use of the article 1 is located between the two mentioned muscle tendons.

The width M is preferably between 15 and 45 mm, more preferably between 25 and 35 mm. If the width M exceeds about 35 mm, the article 1 is likely to feel uncomfortable for the majority of wearers. If the width M exceeds 45 mm, discomfort and chafing is highly likely to occur due to the higher stiffness of the first region 12.

The head part 13 of the first region 12 in the front portion 2 comprises further two side edges 22, 23, which diverge forwards in the longitudinal direction, i.e. in the forward direction of the article 1, from the transition 5 and at least some way into the front portion 2.

An angle between a line in the longitudinal direction of the article 1 and each of the side edges 22, 23 of the head part 13 has been designated by α in FIG. 1. The angle α is measured where the angle between a line in the longitudinal direction of the article 1 and each of the side edges 22, 23 is largest. In the case of a large angle α, for example close to 90°, the side edges 22, 23 in the front portion 2 may chafe against the groins and the legs of the wearer and in this way cause discomfort for the wearer. The smaller the angle α, the greater the risk that the article 1 will slide backwards in between the legs of the wearer. In the case of an angle α of less than 30°, this risk is unacceptably high. An angle α of 40-60° provides the best balance between secure positioning and comfort. An angle α of 45-55° has been found to be especially favourable.

Furthermore, the absorbent core 6 according to an embodiment of the disclosure comprises a second region 24, which surrounds the first region 12 and extends between the first region 12 and the circumferential edge 7. The second region 24 is further constituted by a centre region 25 extending between the facing sides 19, 20 of the legs 15, 16 and an edge region 26. The edge region 26 is preferably >5 mm, more preferably 5-20 mm, in an orthogonal direction from said circumferential edge 7. According to the disclosure, the absorbent core 6 has a lower density in the second region 24 than in the first region 12. That is, the average density of the absorbent core 6 in the second region 24 is lower than the average density of the absorbent core 6 in the first region 12.

Preferably, the second region 24 has a lowest density which is at least 20% lower, more preferably at least 30% lower and most preferably at least 50% lower than the density of the first region 12. For example, if the absorbent material of the core is fluff pulp, the density of the fluff pulp in the first region 12 is preferably 120-200 kg/m$^3$, more preferably 150-170 kg/m$^3$, and the density of the fluff pulp in the second region 24 is preferably 50-100 kg/m$^3$, more preferably 70-90 kg/m$^3$.

The exemplified density ranges for the first region 12 and the second region 24 imply that the first region 12 and the second region 24 are provided with different stiffness. If another absorbent material than fluff pulp is utilized for the core 6, the same different stiffness of the first region 12 and the second region 24 may be provided by other densities of the first and second regions 12, 24.

Furthermore, if the absorbent material comprises a superabsorbent polymer (SAP), the weight and volume of SAP are omitted when the density of the first and second regions 12, 24 is calculated in the context of the present disclosure. This is due to the fact that SAP has a relatively high density, but does not contribute to the stiffness of the first and second regions 12, 24.

As above mentioned, the second region 24 is divided into a centre region 25 and an edge region 26. The density of the centre region 25 and the edge region 26 may be the same or different. Furthermore, the density within each of the first region 12, the centre region 25 and the edge region 26 may vary or be constant.

According to the disclosure, the thickness of the centre region 25 is greater than the thickness of the first region 12. The thickness of the edge region 26 may be greater than the thickness of the first region 12 or may be the same. This is further described below when two different manufacturing methods are described.

Material should be present in the lower density regions 25, 26—the situation in which the density of the lower density regions 25, 26 is zero is not comprised within the scope of this disclosure.

A number of methods for measuring the density of absorbent cores, or the average density of samples, have been described in the literature. In particular, the average density of a sample of absorbent core may be measured according to the following procedure:

The absorbent article is carefully delaminated: any inner or outer coversheets are removed so as to only leave a unitary core.

A pressure of 0.5 kPa is applied to the absorbent core via a foot which corresponds in area to the area of the sample of absorbent core for which the density is to be measured The thickness of the sample is measured while subject to this pressure.

The samples for which densities are to be calculated are cut out from the core, and the surface weight (g/cm$^2$) of these samples is calculated from their mass/surface area.

From the surface weight and the thickness, the average density of these areas is calculated. The average density (kg/m$^3$) is calculated by dividing the surface weight by the thickness.

The geometrical design of the first region 12 and the density difference, i.e. the stiffness difference, between the first and second regions 12, 24 promote formation of an advantageous 3-dimensional form of the article 1 when it is used. The advantageous 3-dimensional form provides a very good anatomical adaptation of the article 1, i.e. a good fit of the article 1 is provided. In addition, stability of the article 1 in the fitted position on the wearer is provided. Stability of the article 1 is provided, for example, by the high density of the first region 12.

In use, the transition 5 of the absorbent article 1 is positioned between the two mentioned muscle tendons. Then transverse compression of the longitudinal edges 8, 9 between the tendons due to the lower density of the edge region 26 promotes formation of the correct 3-dimensional form of the article 1. In particular, the transverse compression of the longitudinal edges 8, 9 between the tendons allows the front portion 2 of the article 1 to fold upwards towards the user and a "bowl" shape can be formed. This allows closer, more secure fit of the article 1. Predetermined shaping of the article 1 also reduces the risk of the article folding in an undesired manner, for example creating channels which may cause leakage.

Furthermore, in that the width M of the first region 12 in the transition 5 essentially corresponds to the distance between the two mentioned muscle tendons on the wearer and in that the two side edges 22, 23 of the head part 13 of the first region 12 diverge forwards in the longitudinal direction from the transition 5, the absorbent article 1 will during use be anchored firmly with the transition 5 between the muscle tendons and be retained in this position. The front portion 2 of the article 1 is therefore held in the area in front of the mentioned muscle tendons, while the crotch portion 3 of the article 1 is positioned correctly against the genitals of the wearer. This helps to avoid problems associated with incorrect placement of the absorbent article 1, or movement of the article 1 during wear. In this way, the article 1 is prevented from moving backwards between the legs of the wearer. Even though a sanitary towel is fastened to the underwear in use, this is a common problem in conventional sanitary towels because the leg movements of the wearer often shift the sanitary towel backwards.

As the centre region 25 is thicker than the first region 12 according to an embodiment of the disclosure, the centre region 25 provides a preformed raised portion, i.e. a preformed hump is provided. In addition, due to the fact that the density of the absorbent core 6 is lower in the centre region 25 than in the first region 12 and the fact that the facing sides 19, 20 of the respective legs 15, 16 converge backwards in the longitudinal direction of the article 1, the absorbent article 1 folds in use along the longitudinal centre line A in at least parts of the crotch portion 3 and the rear portion 4.

Thereby, the preformed raised portion in the centre region 25 is further enhanced during use in at least parts of the crotch portion 3 and the rear portion 4. The hump is intended to make contact with the genitals of the wearer during use of the article 1. Discharged bodily fluid can in this way be caught as soon as it leaves the body of the wearer and be absorbed immediately into the article 1 instead of running out over the surface of the latter.

Furthermore, the hump in the rear portion 4 is accommodated in the cleft between the user's buttocks. This reduces the leakage from the rear of the article 1. More specifically, it provides very good protection against leakage via the cleft between the buttocks, which type of leakage usually occurs during the use of conventional absorbent articles when the user is lying on her back.

Promoting a certain fold or hump in the rear portion 4 increases the comfort of absorbent articles, as undesired twisting, bunching or Z-folding of the article between the buttocks is reduced. Folding of the rear portion 4 between the user's buttocks also promotes secure fit, as transverse and longitudinal movement of the article during wear is reduced.

Thus, the parts of the lower density edge region 26 intended to be positioned between the two mentioned muscle tendons, the width M of the first region 12 at the transition 5, the design of the facing sides 19, 20 of the two legs 15, 16 and the density difference between the first region 12 and the second region 24 cooperate in order to provide the article with a form that follows the contours of the wearer's body even more closely. More specifically, the article is provided with a form that moulds around labia during use.

A further effect of the regions 25, 26 of lower density is that they have larger pores and capillaries and therefore lower capillary action than the first region 12. A capillary gradient is therefore present in the article 1, so that liquid is distributed more preferentially into the denser (non-soft) areas, i.e. into the first region 12. This leads to an article 1 having improved security against leakage, as liquid will not be distributed into the lower density areas as much as the denser areas. For example, the less dense edge region 26 will function as a barrier along the edges of the core. Furthermore, due to the structure of large pores in the centre region 25, the permeability becomes high and provides faster inlet of liquid.

Furthermore, the lower density regions 25, 26 may have, for example, a variable density which increases gradually towards the edges of said regions such that it reaches 100% at the edges of the regions where they meet the first region 12. This allows a wider range of fit, as users with a narrower crotch will be able to compress the lower density regions 25, 26 more, while those with wider crotches will compress the lower density regions 25, 26 less. The articles 1 will therefore fit the minority of people who do not have the above-mentioned ranges of the distance between the two muscle tendons. Additionally, the density gradient in these regions 25, 26 results in an absorption gradient, as lower density material has a lower capillary action. This provides additional security against leakage at the edges of the article 1, as the absorption properties of the article 1 decrease in the edge region 26 towards the edges and fluid is directed towards the first region 12 of the article 1. Furthermore, this provides additional direction of liquid in the centre region 25 towards the first region 12, as the absorption properties of the article 1 increase in the centre region 25 towards the first region 12.

The article 1 according to an embodiment of the disclosure is also provided with soft edges due to the fact that the edge region 26 has low density. The soft edges increase comfort.

In addition, the higher density of the first region 12 implies that it has great liquid-spreading capacity for rapid spreading of bodily fluid received from the wearer over the core 6. The higher density of the first region 12 in the head part 13 also promotes stability, i.e. it promotes that the head part 13 remains out-stretched and that wrinkle formation is inhibited.

Figure 2:
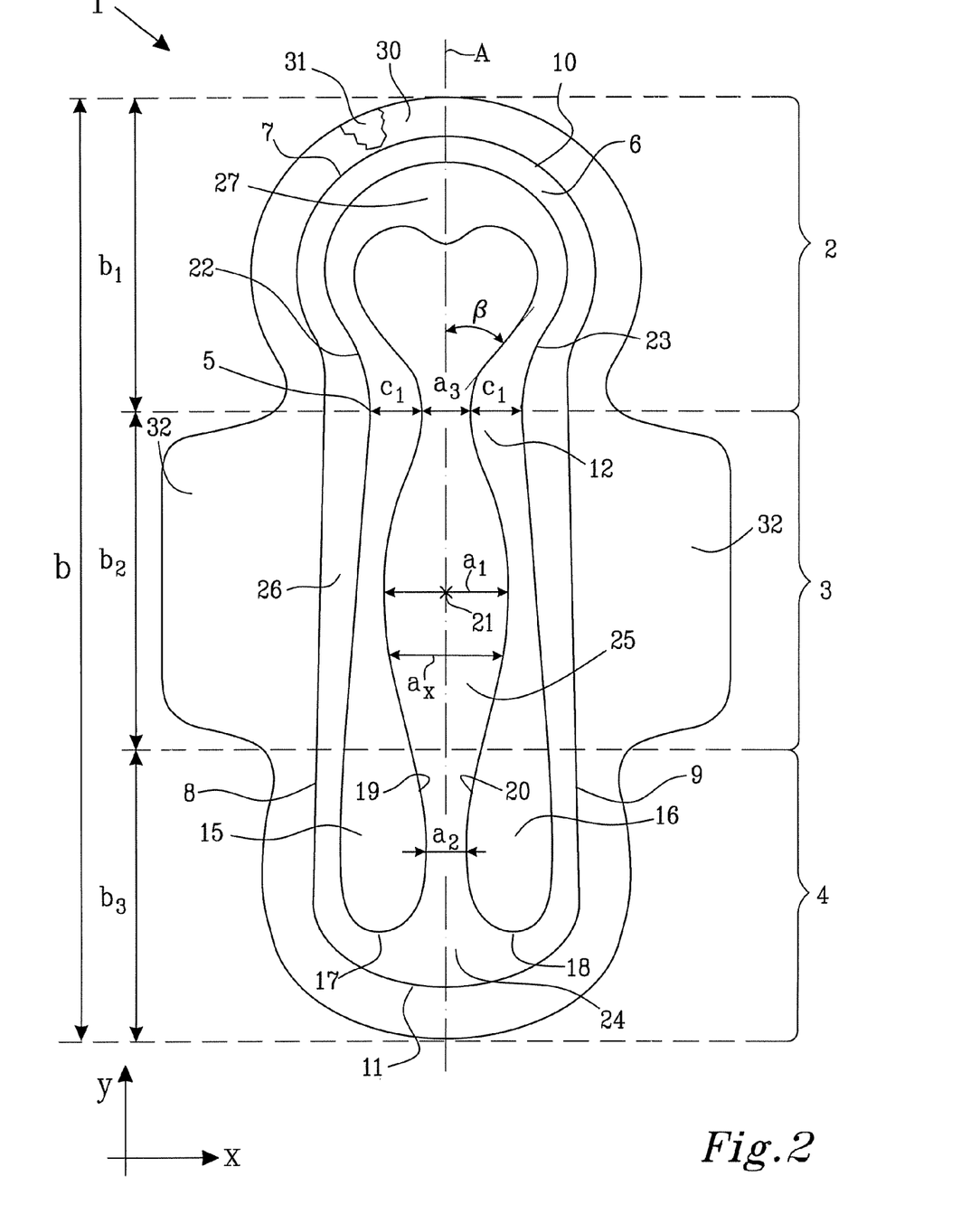
FIG. 2 shows a plan view of a second embodiment of the absorbent article according to the disclosure.

FIG. 2 shows a plan view of a second embodiment of the absorbent article 1 according to the disclosure. The second embodiment corresponds to the first embodiment shown in FIG. 1 except concerning the design of parts of the first region 12, or more specifically, the extension of the legs 15, 16. In the second embodiment, the first region 12 comprises the two legs 15, 16 and a leg joining part 27 in the front portion 2. The two legs 15, 16 extend from the leg joining part 27 in the front portion 2, through the crotch portion 3 towards the separate leg endings 17, 18 in the rear portion 4. Thus, in the second embodiment the two legs 15, 16 extend through at least parts of the front portion 2, through the entire crotch portion 3 and through at least parts of the rear portion 4 in the longitudinal direction. However, in spite of the fact that the extension of the legs 15, 16 in the second embodiment differs from the first embodiment, the design of the first region 12 does not differ backwards in the longitudinal direction from a position corresponding to the position of the crotch point 21.

In the second embodiment shown in FIG. 2, the facing sides 19, 20 of the respective legs 15, 16 converge forwards in the longitudinal direction such that the distance $a_x$ between the facing sides 19, 20 of the legs 15, 16 in the transverse direction is reduced from the maximum distance $a_1$ in the crotch portion 3 to a minimum transition distance $a_3$ in the transition 5 between the front portion 2 and the crotch portion 3. In other words, the facing sides 19, 20 of the respective legs 15, 16 converge in a forward direction of the article 1 from the position in the longitudinal direction where the maximum distance $a_1$ is located to a position in the transition 5.

For example, the minimum transition distance $a_3$ may be <25 mm. Preferably, the minimum transition distance $a_3$ is 5-20 mm and most preferably $a_3$ is 5-15 mm.

Furthermore, each leg 15, 16 has a width $c_1$ in the transition 5. The total width of the two legs 15, 16 in the transition 5, i.e. $c_1+c_1$, corresponds to the width M of the first region 12 in the first embodiment. Therefore, the total width of the two legs 15, 16 is preferably between 15 and 45 mm, more preferably between 25 and 35 mm.

In addition, the facing sides 19, 20 of the respective legs 15, 16 diverge forwards in the longitudinal direction from the transition 5 and at least some way into the front portion 2, i.e. until they meet the leg joining part 27. An angle between a line in the longitudinal direction of the article 1 and each of the facing sides 19, 20 in the front portion has been designated by β in FIG. 2. The angle β is measured where the angle between a line in the longitudinal direction of the article 1 and each of the facing sides 19, 20 is largest. For example, β may be 35°-55°. An angle β of 45° is favourable.

In addition to the advantages provided by the first embodiment, the second embodiment further provides the advantage of an even greater centre region 25 having low density. Especially if the core 6 has a relatively high basis weight, the first region 12 in the front part 2 of the first embodiment can become too stiff. In this case the second embodiment can be preferable as the first region 12 covers a smaller area in the front part 2. The front part 2 is more flexible in the second embodiment than in the first embodiment. Still the first region 12 in the second embodiment provides similar advantages as in the first embodiment.

Furthermore, in some conditions during use, the region of liquid inlet can be rather far to the front part 2. In this case it is an advantage if the fast inlet property of the core region 25 is included in the front part 2, which is the case in the second embodiment. In addition, a raised portion is formed in the region of $a_3$ in the second embodiment, which provides closer contact with the body in this area and, thus, higher leakage security.

Figure 3:
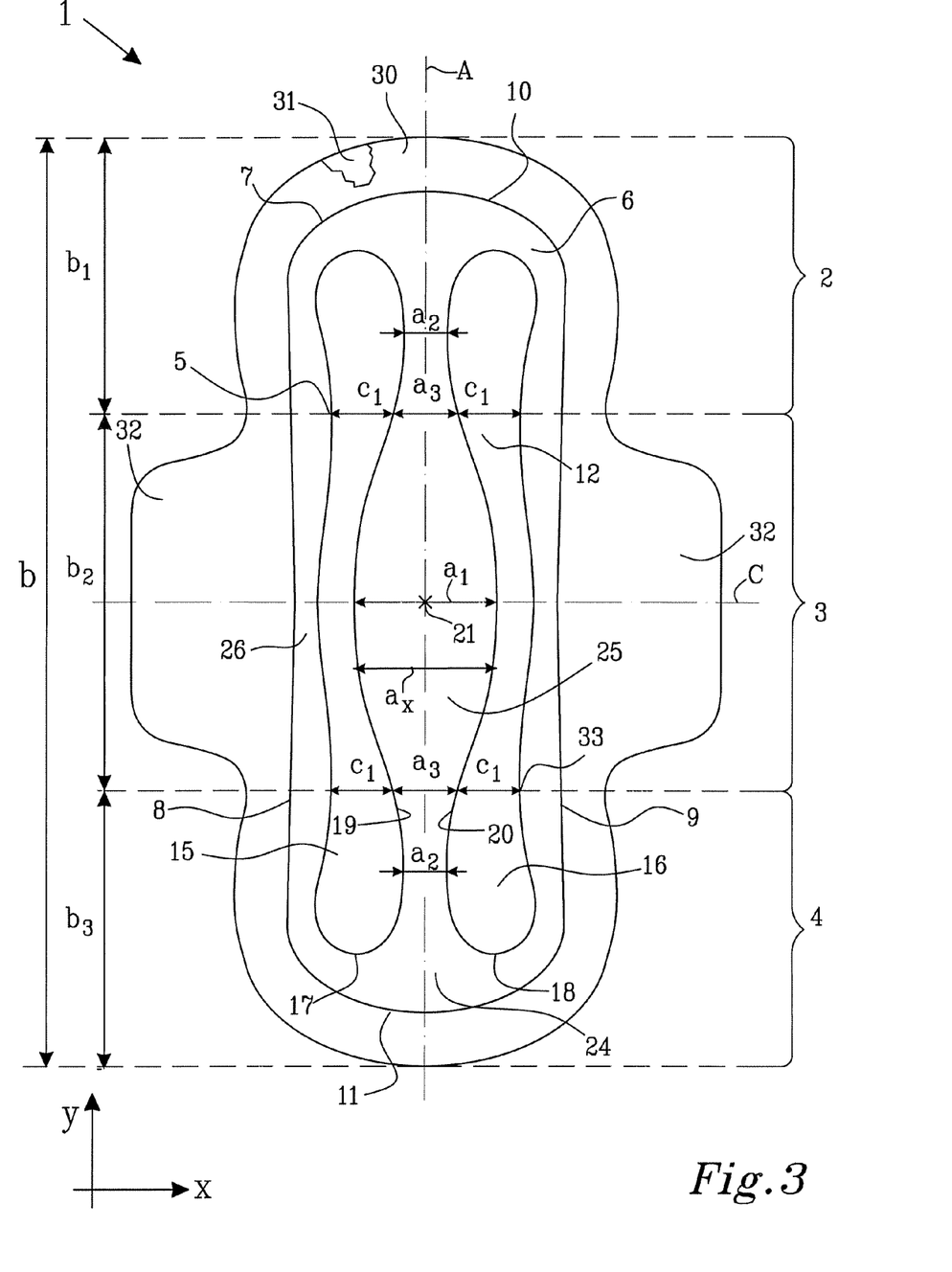
FIG. 3 shows a plan view of a third embodiment of the absorbent article according to the disclosure.

FIG. 3 shows a plan view of a third embodiment of the absorbent article 1 according to the disclosure. The third embodiment corresponds to the second embodiment except for concerning the design of the first region 12. Furthermore, the third embodiment is symmetric around a transverse centre line C. Thus, in the third embodiment the length of the portion 2 and the portion 4 are essentially equal. The third embodiment of the article may be used such that the portion 2 covers the pubic regions of the wearer and such that the portion 4 extends towards the user's rear. Alternatively, the third embodiment of the article may be used such that the portion 4 covers the pubic regions of the wearer and such that the portion 2 extends towards the user's rear.

In the third embodiment, the first region 12 comprises two legs 15, 16, which are totally separated from each other. The two legs 15, 16 are arranged symmetrically around the longitudinal centre line A. Furthermore, the two legs 15, 16 are related to each other such that at reflection in a plane located on the longitudinal centre line A, each leg 15, 16 is the mirror image of the other leg 15, 16.

Furthermore, in the third embodiment, a maximum distance $a_1$ in the transverse direction between the facing sides 19, 20 of the respective legs 15, 16 is, in the crotch portion 3, located at a position in the longitudinal direction of the article corresponding to a position of a crotch point 21. In addition, the facing sides 19, 20 of the respective legs 15, 16 converge backwards in the longitudinal direction of the article 1 from the maximum distance $a_1$ in the crotch portion 3 such that the distance $a_3$ is formed in a transition 33 between the crotch portion 3 and the portion 4, and such that the minimum distance $a_2$ is formed in the portion 4.

Furthermore, in the third embodiment, the facing sides 19, 20 of the respective legs 15, 16 converge forwards in the longitudinal direction of the article 1 from the maximum distance $a_1$ in the crotch portion 3 such that the distance $a_3$ is formed in the transition 5 between the crotch portion 3 and the portion 2 and such that the minimum distance $a_2$ is formed in the portion 2.

The distances $a_1$, $a_2$ and $a_3$ correspond to those given above for the first and second embodiments.

Figure 4A:
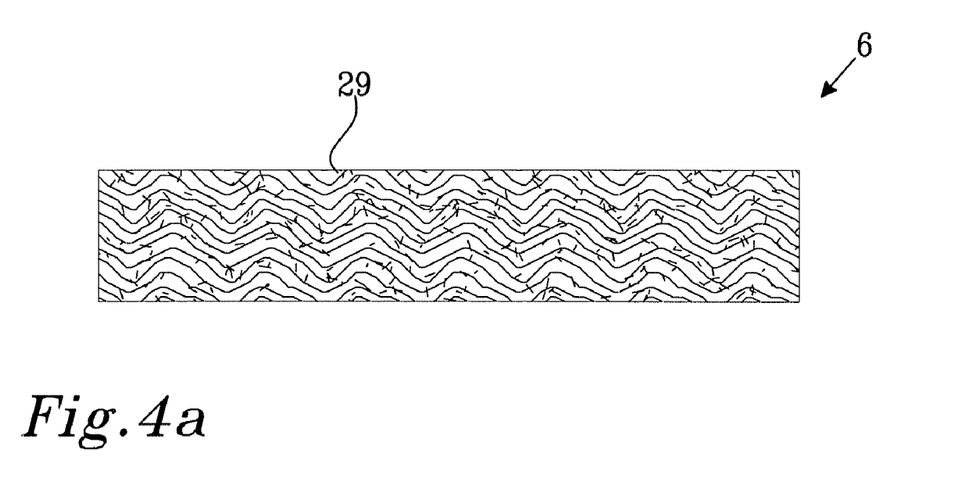
FIGS. 4a-b illustrate schematically one method by which absorbent cores according to the present disclosure may be produced.
Figure 4B:
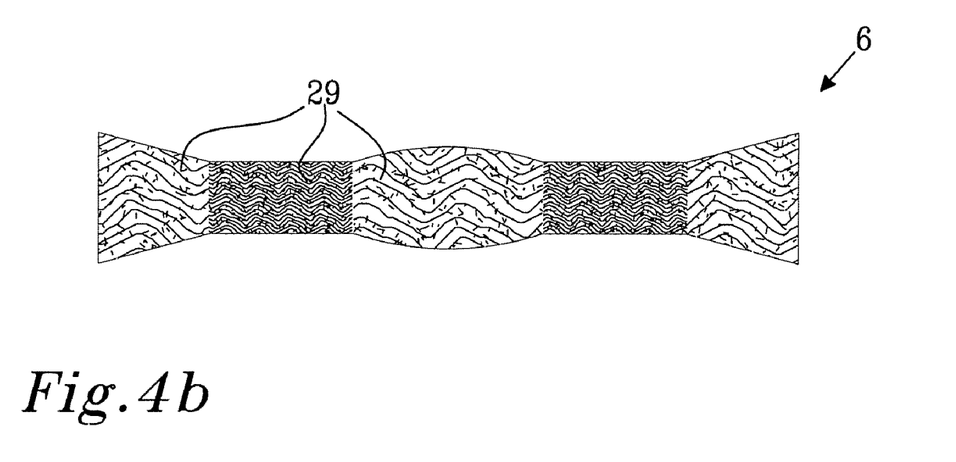

A suitable technique for forming the absorbent cores 6 of the present disclosure is mat-forming through an air-laying process, as schematically illustrated in FIGS. 4a-b and as described more closely in EP-A2-1 253 231. In the embodiment shown in FIGS. 4a-b, an air-permeable mould (not shown) having a uniform depth is provided. Fibrous material 29 is air-laid into the mould and the mould is filled, whereby an absorbent core 6 is produced in which the amount of fibrous material 29 at each point is the same (FIG. 4a).

After the absorbent core 6 is produced, it is pattern-compressed so that an absorbent core 6 having regions with different densities is produced (FIG. 4b). Compressing may take place using any known means.

Furthermore, in this embodiment the density of the fibrous material in the non-compressed absorbent core 6 (FIG. 4a) corresponds to the density of the absorbent core 6 in the regions of lower density according to the disclosure. The absorbent core 6 outside these regions is then compressed while within these regions, the core 6 remains uncompressed (FIG. 4b).

In the efficient mat-forming processes of today, mat-forming wheels are used, as described in U.S. Pat. No. 4,765,780, SE 9401542-7 and EP-A2-1 253 231. The air-permeable moulds are evenly spaced about the periphery of the mat-forming wheels. Fibrous material (together with any other material which might be desired) is fed from mills by means of blowers and onto mat-forming wheels via mat-forming covers. More than one mat-forming cover may be present per forming wheel and the concentration of the various components could differ in the different covers.

In an alternative to forming in mat-forming wheels, the absorbent cores 6 of the present disclosure may be produced by laying fibrous material (together with any other material which might be desired) onto a web having a profile which ultimately gives a density difference on different parts of the material web. The material can be prefabricated and rolled up into rolls.

Figure 5A:
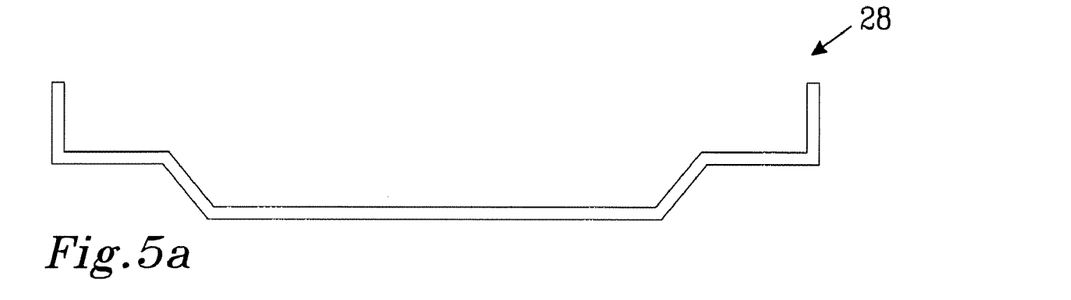
FIGS. 5a-d illustrate schematically an alternative method by which absorbent cores according to the present disclosure may be produced.
Figure 5B:
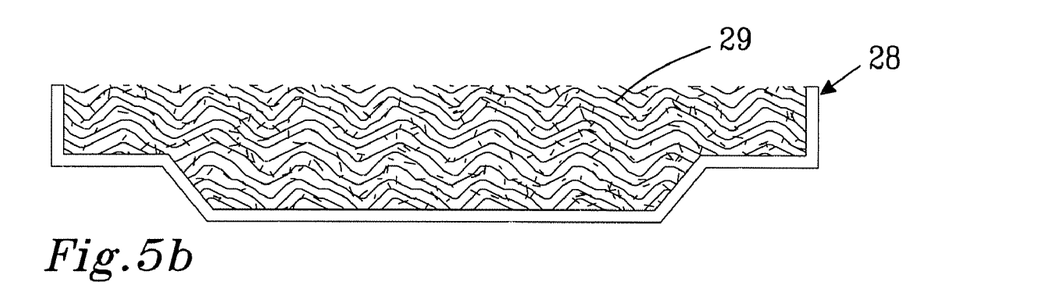
Figure 5C:
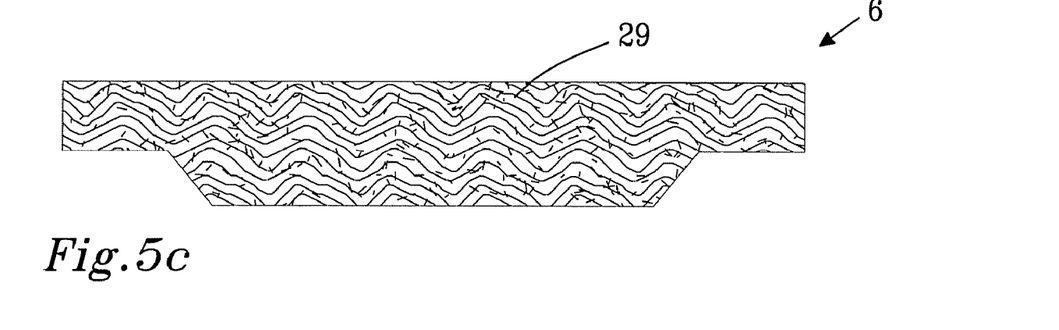

In an alternative embodiment, an absorbent core 6 according to the present disclosure is produced as schematically illustrated in FIGS. 5a-d. An air-permeable mould 28 having the desired shape is provided. The depth of the mould 28 can vary, as seen in the cross-sectional view in FIG. 5a, according to the amount of material which is required at each point. Fibrous material 29 is air-laid into the mould 28, and the mould 28 is filled (see FIG. 5b). Due to the differences in the mould depth in various areas, the amount of fibrous material at some points will vary (FIG. 5c).

Figure 5D:
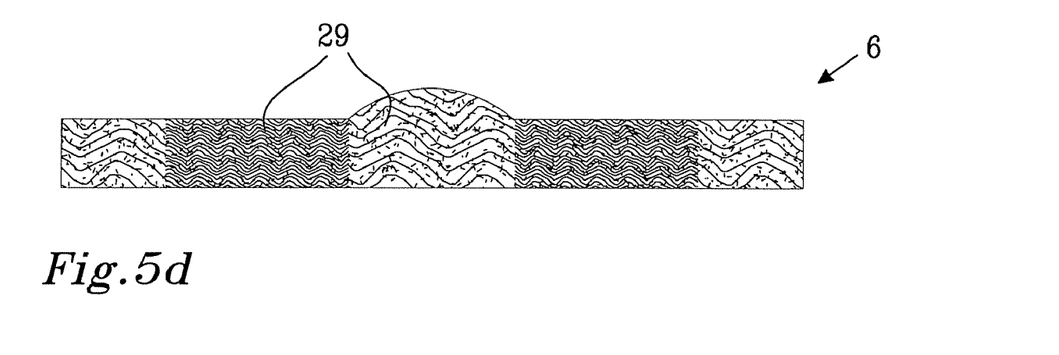

After the absorbent core 6 is produced, it is compressed in those regions corresponding to the first region 12 and the edge region 26 so that a uniform thickness is obtained in those regions. Thus, after the compression the thickness of the centre region 25 is greater than the thickness of the first region 12 and the edge region 26 (FIG. 5d).

In this way, areas of different densities can be built up within the absorbent core 6. If desired, masks or baffles may be introduced in the mat-forming process, so that fibre-laying in the unmasked areas is higher than in the masked areas. Alternatively, the moulds may have different hole density and/or hole size in different areas of the mould. The flow of fibrous material will therefore be different in different areas of the mould. This allows further control over the material density.

In addition to the absorbent core 6, the absorbent article 1 according to the disclosure may comprise, as shown in FIGS. 1-3, an inner coversheet 30 and an outer coversheet 31. The inner coversheet 30 lies in direct contact with the wearer's body, and should therefore be soft, comfortable and liquid-permeable. The inner coversheet 30 can comprise a non-woven material, e.g. spunbond, meltblown, carded, hydroentangled, wetlaid etc. Suitable nonwoven materials can be composed of natural fibres, such as wood pulp or cotton fibres, manmade fibres, such as polyester, polyethylene, polypropylene, viscose etc. or from a mixture of natural and man-made fibres. The inner coversheet material may further be composed of tow fibres, which may be bonded to each other in a bonding pattern, as e.g. disclosed in EP-A-1 035 818. Further examples of inner coversheet materials are porous foams, apertured plastic films etc. The materials suited as inner coversheet materials should be soft and non-irritating to the skin and be readily penetrated by body fluid, e.g. urine or menstrual fluid. The inner coversheet 30 may further be different in different parts of the absorbent article 1.

The outer coversheet 31 lies in contact with the wearer's garments, and is liquid-impermeable. The outer coversheet 31 refers to the liquid impervious material forming the outer cover of the absorbent article 1. The outer coversheet can comprise a thin plastic film, e.g. a polyethylene or polypropylene film, a nonwoven material coated with a liquid impervious material, a hydrophobic nonwoven material, which resists liquid penetration, or a laminate of a plastic film and a nonwoven material. Other laminate materials which are suitable for use as the outer coversheet are laminates of a nonwoven material and high-loft wadding material. The outer coversheet material may be breathable so as to allow vapour to escape from the absorbent core, while still preventing liquids from passing therethrough. Examples of breathable outer coversheet materials are porous polymeric films, nonwoven laminates of spunbond and meltblown layers and laminates of porous polymeric films and nonwoven materials. Preferably, the outer coversheet 31 comprises nonwoven material in at least the garment-facing surface thereof.

In the embodiments shown in FIGS. 1-3, the inner coversheet 30 and the outer coversheet 31 extend with edge portions outside the absorbent core 6 around the latter and are interconnected along these edge portions to form a cover around the absorbent core 6. The cover formed by the inner and outer layers extends outwards in the transverse direction to form flexible side flaps 32 or "wings", in the region of the crotch portion 3. The side flaps 32 are intended to be arranged around the crotch portion on the briefs of the wearer. Furthermore, the side flaps 32 are suitably provided with adhesive coating (not shown) on the outer coversheet 31, by means of which the wings 32 can be attached around the legs of the briefs.

However, even if the absorbent article 1 shown in FIGS. 1-3 comprises wings 32, the absorbent article 1 may in variants of those embodiments not comprise any wings.

Furthermore, in an alternative embodiment, the absorbent article 1 may only comprise an outer coversheet 31, i.e. no inner coversheet. Additionally, the absorbent core 6 of the absorbent article may be wrapped in a single coversheet which can act as both inner and outer coversheet.

The absorbent article 1 may further include an acquisition distribution layer (not shown) which is placed on top of the absorbent core 6 and adapted to quickly receive and temporarily store discharged liquid before it is absorbed by the absorbent core 6. Such acquisition distribution layers are well known in the art and may be composed of porous fibrous wadding, SD plastic film, LDA (low density airlaid), multi-bond, latex bonded or foam materials.

A sanitary towel 1 according to the disclosure may comprise any attachment means known in the art to allow fastening to undergarments of a wearer. Such means may include a coating of adhesive or friction coating on the garment-facing surface of the article. Furthermore, the article 1 according to the disclosure may comprise, as above described, attachment flaps ("wings") which extend in the transverse direction of the article 1 and are intended to be arranged around the crotch portion on the briefs of the wearer. It is however important that the nature and placement of such attachment means does not significantly interfere with the function of the article 1 in use.

Although the above discussion has been exemplified through a sanitary napkin, the present disclosure is also applicable to other absorbent articles such as diapers, incontinence pads or panty-liners. For instance, application of the invention to diapers would provide similar benefits in terms of comfort, fit and leakage-prevention.

The invention should not be considered as limited by the above description; rather the scope and limitations of the invention are defined by the granted claims, and equivalents there.

The invention claimed is:

1. An absorbent article, whereby said article has a transverse direction, a longitudinal direction and a longitudinal centre line, whereby said article further has a front portion, a crotch portion and a rear portion, whereby said article comprises an absorbent core of unitary construction, whereby said absorbent core is delimited by a circumferential edge, whereby said absorbent core comprises a first region extending in the longitudinal direction of the article from a position in the front portion, through the crotch portion and at least some way into the rear portion, whereby said first region comprises two legs extending in the longitudinal direction of the article through at least parts of the crotch portion towards separate leg endings in the rear portion, whereby said legs are arranged symmetrically about said longitudinal centre line, whereby a distance between facing sides of the respective legs in the transverse direction varies in the longitudinal direction, whereby a maximum distance between the facing sides of the respective legs in the transverse direction is, in the crotch portion, located at a position in the longitudinal direction corresponding to a position of a crotch point, whereby said facing sides of the respective legs converge backwards in the longitudinal direction such that said distance is reduced from said maximum distance to a minimum distance in the rear portion, whereby said absorbent core further comprises a second region surrounding said first region and extending between said first region and said circumferential edge, and whereby the average density of said absorbent core in said second region is lower than the average density of said absorbent core in said first region.

2. The absorbent article according to claim 1, wherein said facing sides of the respective legs converge forwards in the longitudinal direction such that the distance between said facing sides of the respective legs is reduced from said maximum crotch portion distance to a zero distance in the crotch portion.

3. The absorbent article according to claim 2, wherein a width of said first region at a transition between said front portion and said crotch portion is in the order of 15-45 mm in the transverse direction.

4. The absorbent article according to claim 1, wherein said facing sides of the respective legs converge forwards in the longitudinal direction such that the distance between said facing sides of the respective legs in the transverse direction is reduced from said maximum crotch portion distance to a minimum transition distance in a transition between said front portion and said crotch portion.

5. The absorbent article according to claim 4, wherein a total width of said first region in said transition between said front portion and said crotch portion is in the order of 15-45 mm in the transverse direction.

6. The absorbent article according to claim 4, wherein said minimum transition distance is less than 25 mm.

7. The absorbent article according to claim 4, wherein said facing sides of the respective legs diverge forwards in the longitudinal direction from said transition and at least some way into the front portion.

8. The absorbent article according to claim 1, wherein said maximum crotch portion distance is 10-50 mm.

9. The absorbent article according to claim 1, wherein said minimum distance in said rear portion is 5-30 mm.

10. The absorbent article according to claim 1, wherein said second region is constituted by a centre region extending between said facing sides of said legs and an edge region, whereby said edge region is greater than 5 mm in an orthogonal direction from said circumferential edge.

11. The absorbent article according to claim 2, wherein said maximum crotch portion distance is 10-50 mm.

12. The absorbent article according to claim 4, wherein said maximum crotch portion distance is 10-50 mm.

13. The absorbent article according to claim 2, wherein said minimum distance in said rear portion is 5-30 mm.

14. The absorbent article according to claim 4, wherein said minimum distance in said rear portion is 5-30 mm.

15. The absorbent article according to claim 2, wherein said second region is constituted by a centre region extending between said facing sides of said legs and an edge region whereby said edge region is greater than 5 mm in an orthogonal direction from said circumferential edge.

16. The absorbent article according to claim 4, wherein said second region is constituted by a centre region extending between said facing sides of said legs and an edge region whereby said edge region is greater than 5 mm in an orthogonal direction from said circumferential edge.

17. The absorbent article according to claim 1, wherein the first region extends continuously in the longitudinal direction of the article from the position in the front portion, through the crotch portion and at least some way into the rear portion.

\* \* \* \* \*